US011331110B2

(12) United States Patent
Boger et al.

(10) Patent No.: US 11,331,110 B2
(45) Date of Patent: May 17, 2022

(54) OSCILLATING DECORTICATION BURR ASSEMBLY

(71) Applicants: David K. Boger, Sonoma, CA (US); William Krauss, Birmingham, AL (US)

(72) Inventors: David K. Boger, Sonoma, CA (US); William Krauss, Birmingham, AL (US)

( * ) Notice: Subject to any disclaimer, the term of this patent is extended or adjusted under 35 U.S.C. 154(b) by 103 days.

(21) Appl. No.: 16/858,040

(22) Filed: Apr. 24, 2020

(65) Prior Publication Data

US 2020/0246022 A1 Aug. 6, 2020

Related U.S. Application Data

(63) Continuation of application No. 16/019,045, filed on Jun. 26, 2018, now Pat. No. 10,631,882, which is a continuation-in-part of application No. 15/499,267, filed on Apr. 27, 2017, now Pat. No. 10,617,433.

(60) Provisional application No. 62/328,945, filed on Apr. 28, 2016.

(51) Int. Cl.
*A61B 17/32* (2006.01)
*A61B 17/16* (2006.01)
*A61B 17/56* (2006.01)

(52) U.S. Cl.
CPC ........ *A61B 17/1659* (2013.01); *A61B 17/162* (2013.01); *A61B 17/1617* (2013.01); *A61B 17/1628* (2013.01); *A61B 17/1682* (2013.01); *A61B 17/1686* (2013.01); *A61B 2017/564* (2013.01)

(58) Field of Classification Search
CPC ............ A61B 17/1659; A61B 17/1617; A61B 17/162; A61B 17/1682; A61B 17/1686; A61B 17/1628; A61B 2017/564

USPC .............. 606/79–85; 433/119, 86, 165–166, 433/141–164, 51

See application file for complete search history.

(56) References Cited

U.S. PATENT DOCUMENTS

| | | | | |
|---|---|---|---|---|
| 5,538,425 A | * | 7/1996 | Reeves | A61C 1/05 433/126 |
| 5,743,918 A | * | 4/1998 | Calandruccio | A61B 17/1615 128/898 |
| 10,631,882 B2 | * | 4/2020 | Boger | A61B 17/1659 |
| 2003/0157458 A1 | * | 8/2003 | Buchanan | A61C 3/03 433/166 |
| 2005/0142515 A1 | * | 6/2005 | Levy | A61C 17/20 433/114 |
| 2006/0025772 A1 | * | 2/2006 | Leibel | A61B 17/1686 606/915 |
| 2006/0111726 A1 | * | 5/2006 | Felt | A61B 90/06 606/86 R |
| 2007/0275348 A1 | * | 11/2007 | Lemon | A61C 3/03 433/119 |
| 2008/0262476 A1 | * | 10/2008 | Krause | A61B 17/32002 604/540 |
| 2013/0197654 A1 | * | 8/2013 | Samuelson | A61F 2/3886 623/20.35 |
| 2016/0184046 A1 | * | 6/2016 | Blain | A61B 17/1604 600/249 |

(Continued)

*Primary Examiner* — Jessica Weiss
(74) *Attorney, Agent, or Firm* — Erise IP, P.A.

(57) ABSTRACT

An oscillating decorticating burr assembly for decortication of the articular surfaces of joints of the human body is disclosed. The oscillating decorticating burr assembly comprises a burr, a burr-support post, and a handle. Power is imparted to the assembly by way of a user input on the handle causing oscillation of the burr.

19 Claims, 4 Drawing Sheets

(56) References Cited

U.S. PATENT DOCUMENTS

2016/0367372 A1\* 12/2016 Samuelson ......... A61F 2/30767

\* cited by examiner

OSCILLATING DECORTICATION BURR ASSEMBLY

RELATED APPLICATIONS

This patent application is a continuation claiming priority benefit, with regard to all common subject matter, of earlier-filed U.S. Non-Provisional patent application Ser. No. 16/019,045, filed Jun. 26, 2018, and entitled "OSCILLATING DECORTICATION BURR ASSEMBLY" ("the '045 application"), to be issued as U.S. Pat. No. 10,631,882. The '045 application is a continuation-in-part application claiming priority benefit, with regard to all common subject matter, of earlier-filed U.S. Non-Provisional patent application Ser. No. 15/499,267, filed Apr. 27, 2017, and entitled "OSCILLATING DECORTICATION BURR ASSEMBLY" ("the '267 application"), now U.S. Pat. No. 10,617,433. The '267 application is a non-provisional patent application claiming priority benefit, with regard to all common subject matter, of earlier-filed U.S. Provisional Patent Application No. 62/328,945, filed Apr. 28, 2016, and entitled "OSCILLATING DECORTICATION BURR ASSEMBLY." The identified earlier-filed patent applications are hereby incorporated by reference in their entirety into the present application.

BACKGROUND

1. Field

Embodiments of the invention relate to the decortication of the articular surfaces of joints in the human body.

2. Related Art

Various joints within the human body, especially smaller joints such as within the hand and foot, can become arthritic secondary to multiple causes. The arthritis of these joints can cause significant pain and disability. The pain can restrict the ability to perform daily functions such as walking or grasping objects. One of the primary treatments for small joint arthritis is arthrodesis (fusion) of the arthritic joint. In an arthrodesis of a joint, the goal of the surgery is to remove the arthritic joint and allow the two adjacent bones to grow into one continuous bone. Before an arthrodesis can occur, the articular cartilage on the ends of the two adjacent joints must be removed. By removing the articular cartilage and a small amount of subchondral bone directly beneath the cartilage, a high rate of fusion can be achieved.

Traditionally, medical practitioners have removed the articular cartilage and subchondral bone by using a rotary cutting technique or an oscillating saw or high speed burr or hand tools. In the traditional technique, the medical practitioner removes the articular cartilage and subchondral bone by applying a rotary cutting tool directly to the articular surfaces of each bone. The traditional technique is disadvantageous for several reasons. First, the traditional techniques have a very fast removal rate, which can easily lead to excess material removal of subchondral bone. If excess bone is removed, it can upset the surrounding joint dynamics. Second, the traditional technique can be technically difficult and often requires substantial manipulation and distraction of the joint to expose the articular surface for removal. This can cause trauma to the patient's tissue. Third, the rotatory cutting surfaces are very sharp, and it is not uncommon to have incidental damage to the surrounding soft tissues (skin, tendons, muscle) or to the practitioner's own digits. This can lead a medical practitioner to avoid the procedure, even when it would help the patient.

SUMMARY

Embodiments of the invention solve the above-mentioned problems of the prior art by providing an oscillating decorticating burr for removing the articular cartilage and subchondral bone. The oscillating decorticating burr uses oscillation in lieu of cutting to remove the material. This provides the removal of articular cartilage and subchondral bone at a more controlled pace. This makes the removal of excess material or inadvertent soft tissue damage much less likely. The oscillating decorticating burr also requires less exposure and manipulation of the joint, because the oscillating decorticating burr can be fit substantially within the joint space with minimal distraction or manipulation. The oscillating burr can remove the articular cartilage and subchondral bone from both sides of the joint simultaneously thus saving time, preserving the normal contour of the joint and improving the fit of the prepared surfaces.

Finally, the oscillating decorticating burr is relatively easy to operate in comparison with the rotary cutting tool, due in part to the more controlled removal and less manipulation required.

A first embodiment of the invention addresses the above-described needs by providing for an oscillating decorticating burr assembly for removing the articular cartilage and subchondral bone comprising a burr for removing the cortical material from the bone at a joint, a burr-support post fixed to the burr and a handle fixed to the burr-support post that a practitioner may grip that imparts an oscillating motion to the burr.

A second embodiment of the invention provides for an oscillating decorticating burr assembly for removing the articular cartilage and subchondral bone comprising a burr permanently attached to a burr-support post for removing cortical material from the bone at a joint, a handle, attached to the burr-support assembly, for imparting an oscillating motion on the burr, wherein the handle comprises a user input for powering the assembly and for adjusting an oscillation speed imparted on the burr.

A third embodiment is disclosed providing a method for removing the articular cartilage and subchondral bone by decortication comprising securing a burr and burr-support post to a handle, wherein the burr is based on a size and a shape of the joint to be decorticated and the burr-support post is attached to a handle, powering the burr to oscillate by manipulating a user input on the handle and placing the oscillating burr against a joint surface for removing a material from the joint.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
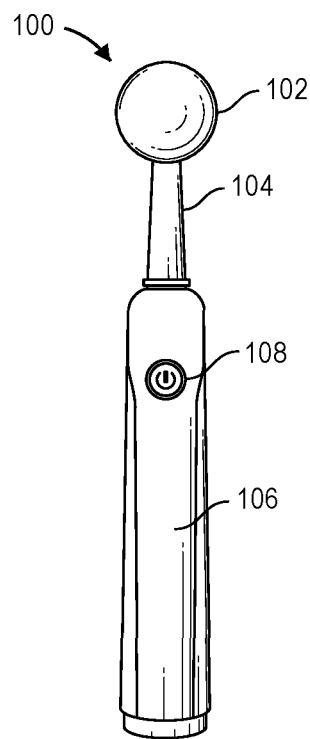
FIG. 1 depicts an exemplary embodiment of the oscillating decorticating burr.

The drawing figures do not limit embodiments the invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying illustrations that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense.

In this description, references to "one embodiment", "an embodiment", "embodiments", "various embodiments", "certain embodiments", "some embodiments", or "other embodiments" mean that the feature or features being referred to are included in at least one embodiment of the technology. Separate references to "one embodiment", "an embodiment", "embodiments", "various embodiments", "certain embodiments", "some embodiments", or "other embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

As shown in FIG. 1, the oscillating decorticating burr assembly 100 generally includes a burr 102, a burr-support post 104, and a handle 106. The burr 102 is configured to remove the cortical material from the bone at the joint. The burr 102 is configured to oscillate. The burr may be placed on the cortical material while oscillating so as to remove a portion of the material. The burr is secured to a burr-support post 104. The burr-support post 104 attaches the burr 102 to the handle 106. The handle 106 provides the oscillating motion to the burr 102 (by any of the various power methods discussed below). The handle 106 is gripped by the medical practitioner to perform the procedure.

As can be seen in FIG. 1, the burr 102 is secured on the burr-support post 104 to allow the burr 102 to be manipulated into the desired location and orientation. The burr 102 is a partially spherical, hemi-spherical, or other arcuate shape. As shown in FIG. 1, the burr 102 may be a generally flattened hemi-spherical shape. In some embodiments, the burr 102 may present a convex side (as visible in FIG. 1) and a concave side (from a view opposite of FIG. 1, not shown). This may allow the burr 102 to fit within the joint. Depending on the joint or joints, different sizes and shapes of burr 102 may be used. The radii of the burr may closely match the dimensions of the joint to be fused.

The burr 102 presents a roughened surface on both faces. The roughened surface removes the cortical material by oscillating against the surface. The roughened surface is sufficiently durable to remove the cortical material without disintegrating. The burr 102 may also present a notch, a recess, or another structure for receiving and being secured to the burr-support post 104, such as shown in FIG. 1 and described below.

The roughened surface of burr 102 may be formed of various hardened materials. The material used may be durable enough to be used in multiple operations without significant deterioration. The material in this scenario may be thoroughly cleaned and sanitized between operations as to avoid contamination. In embodiments, the material may be a low-cost material that may only last for the duration of one operation. This procedure allows for a disposable burr that does not significantly increase the cost. In this scenario, a new burr per procedure is used which ensures that there is no contamination from previous operations.

Figure 2A:
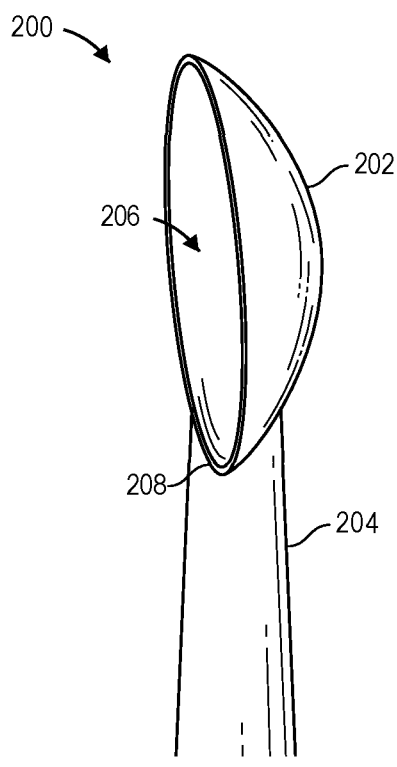
FIGS. 2A and 2B depict an exemplary burr with a concave shape.

In embodiments of the invention, the burr 102 will come in many different sizes and shapes that may be based upon the size and shape or other characteristics of the joint to be fused. For example, the burr 102 may substantially match the size of the joint. This allows the medical practitioner to apply the burr 102 within the joint easily. The medical practitioner may select a burr 102 of a certain outer diameter, thickness and spherical radius. For example, a burr 102 may be 15 mm in diameter and 2 mm thick, such as shown in FIG. 2A. Based upon the joint designed to be used with, the burr 102 may be 5-100 mm in diameter and 1-10 mm in thickness.

The shape of burr 102 may be round, square, triangular, or any shape that may be beneficial to the efficiency of the procedure. In embodiments, the burr 102 may be pointed in the same manner as a dental scraper for better accuracy, or a brush for cleaning. It should therefore be appreciated that various embodiments of the invention may utilize burrs of various sizes, shapes, materials, and configurations to perform various functions.

The burr-support post 104 secures the burr 102 to the handle 106. In embodiments of the invention, the burr 102 is permanently secured to the burr-support post 104. The medical practitioner therefore changes the burr 102 by removing the burr-support post 104 from the oscillating handle 106. In other embodiments, the burr 102 is selectively secured to the burr-support post 104. In these embodiments, the medical practitioner removes the burr 102 from the burr-support post 104 in order to use the correctly-sized burr. The burr 102 may be detachable from the burr-support post 104 and the burr-support post 104 may be detachable from the handle 106 in the same embodiment. In still other embodiments, the burr 102 is a cover configured to be emplaced over a portion of the burr-support post 104. In these embodiments, the burr is slipped onto and off of the burr-support post by the medical practitioner.

It should be appreciated that various embodiments of the burr 102 may be utilized. The size and shape of the burr may depend on the task to be performed, the physical characteristics of the patient, the preferences of the medical practitioner, or other factors. A first exemplary embodiment of the burr 102 is shown in FIG. 1 and described above. This embodiment may be referred to as a convex shape. A second exemplary embodiment of the burr 102 is shown in FIGS.

Figure 3:
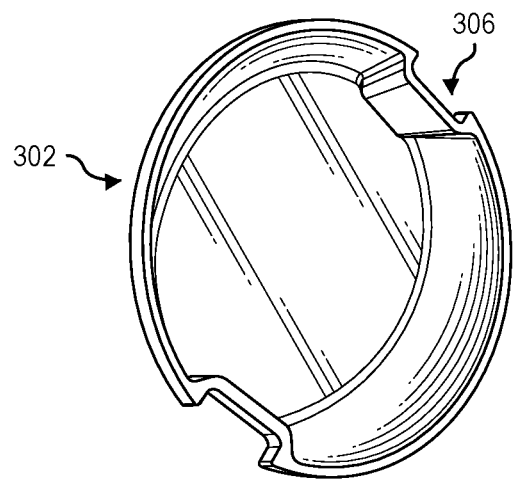
FIG. 3 depicts an exemplary embodiment of the decorticating burr.

2A and 2B. This embodiment may be referred to as a concave shape. A third exemplary embodiment of the burr is shown in FIG. 3. This embodiment may be referred to as a notched shape. The notched shape may be concave (as shown in FIG. 3), convex, flat, or some other shape.

Figure 2B:
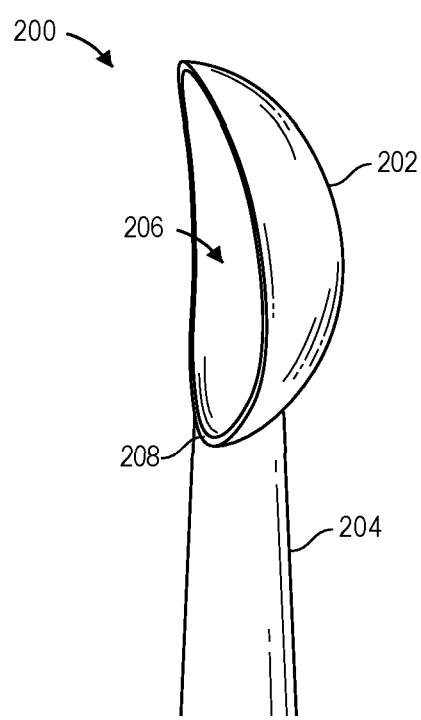

Referring to FIGS. 2A and 2B, a concave burr assembly 200 is shown. The concave burr assembly includes the burr 202 and the burr-support post 204. Like in FIG. 1, the burr 202 and the burr-support post 204 are configured to be secured to the handle 106. The burr 202 presents a recess 206 within the burr 202. The recess is configured to fit around one or more bones of the patient when the burr 202 is disposed within the joint, as discussed more below.

The burr 202 includes a burr wall 208 disposed around the recess 206. The burr wall 208 presents a thickness that is configured to fit within the joint. Because the thickness is less in a concave burr assembly 200 than in the convex shape shown in FIG. 1, the exposure of the joint can be less drastic than prior art systems. In the shown example, the burr wall 208 presents a general arcuate shape. It should be appreciated that in other embodiments, the burr wall 208 may present another shape. For example, the burr wall 208 may present a shape configured to complementarily fit into the joint. This may be in addition to the flexibility of the burr wall 208 that allows the burr wall 208 to flex and fit within the joint.

The flexibility of the burr 202 may provide a benefit of not requiring the medical professional to specify the curvature and other shape characteristics of the joint. This can be advantageous as the joint is not displaced, such that the determination of the size and shape of the joint can be difficult. Thus, a flexible burr 202 allows the burr 202 to conform to the shape of the joint, even if the medical professional does not know what that size and shape are.

In embodiments of the invention, the burr 202 is formed of a sheet of polycarbonate, polyester, acrylic, or other polymer material. These materials make the burr 202 flexible with the recess 206. In some embodiments, the side opposite the recess will be disposed toward the distal end of the finger, such that the recess 206 is fit around the larger of the bones (e.g., the more proximal bone).

FIG. 2A shows the burr 202 in a default position. FIG. 2B shows the burr 202 in a deformed or deflected position. In FIG. 2B a force (not illustrated) is being exerted on the burr 202 that is deforming and/or deflecting the burr 202. Additional external forces may further vary the shape of the burr 202. As such, the burr 202 is flexible so as to conform to external forces, external objects, and the like. For example, as the burr 202 is fit into the joint of the patient (as discussed below), the burr 202 will conform to the shape of the available space between the respective bones.

In addition to flexibility, the burr 202 may include a natural elastic force that returns the burr 202 to the natural shape. For example, when the burr 202 is deformed, such as shown in FIG. 2B, the burr 202 has a tendency to return to the default position. This tendency to return is the elastic force. The elastic force produces a compressive force when disposed within the joint. deformations and deflections of the burr 202 by inserting the burr 202 into the joint provide an equal and opposite force on the joint. This force on the joint emphasizes the decortication at that location.

Figure 4:
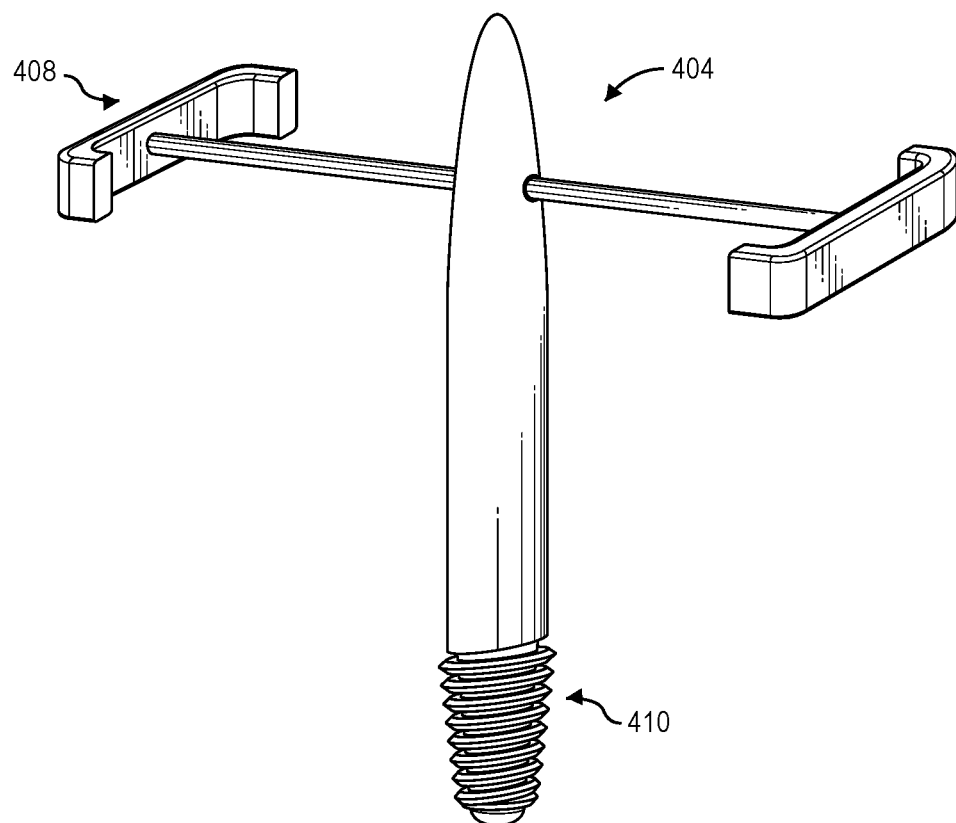
FIG. 4 depicts an exemplary embodiment of the decortication burr assembly.

Referring now to an exemplary embodiment depicted in FIGS. 3 and 4, the interface between the burr 302 and the burr-support post 404 is represented on the burr 302 in FIG. 3 and the burr-support post 404 in FIG. 4. In this embodiment, the burr 302 has two indentions 306. These indentions 306 correspond to hooks 408 on the burr-support post 404. The burr 302 is snapped into the hooks 408 on the burr-support post 404. As such, the burr 302 is retained within the burr-support post 404 and may be selectively removed such that another burr (such as of a different size or shape) may be added.

In embodiments of the invention, various configurations of the burr-support post 404 may be used. As depicted in FIG. 4 a hook 408 may be utilized to grasp the burr. In some embodiments, as depicted, there are two hooks 408 that are each are two sided and configured horizontally, or perpendicular to the burr-support post. In other embodiments of the invention, the hooks 408 are be configured to attach the burr 302 to one side of the burr-support post and the attachments may be configured vertically, or parallel to the burr-support post, not illustrated. The attachment between the burr 302 and the burr-support post 404 may be, but is not limited to, fasteners, clamps, screws, and adhesive. The burr 302 may also be permanently attached to the burr-support post, or molded, or cast as one.

The burr-support post 404 is generally elongated so as to present a distal end and a proximal end. The distal end has attachments for the burr 302 to be disposed thereon. The proximal end includes a handle interface for selectively securing to the oscillating handle 106. In embodiments of the invention, the burr-support post 404 is generally tapered from the proximal end to the distal end. The proximal end (as well as the handle 106) is relatively thick and wide so as to be easily grasped and manipulated by the medical practitioner. The distal end is relatively thin so as to not interfere with the application of the burr to the joint, while providing the structural support necessary to withstand the oscillations and allow for the medical practitioner to exert force against the joint. The distal end may also be telescoping. This may aid the practitioner in reaching the joints and allow the distal end of the burr support post to be slightly narrower.

The burr-support post 404 can be attached to the handle 106 in different ways. In the exemplary embodiment depicted in FIG. 4, the burr-support post has a screw type attachment 410 for screwing into the handle 106 which has a corresponding attachment. The burr-support post 404 may also be attached to the handle 106 by a snapping mechanism, adhesive, or any other method that may be beneficial. The attaching mechanism may be adjustable within the handle 106 housing allowing the burr-support post 404 to be placed at different angles. This may help the practitioner to get the burr 302 into the correct orientation for the procedure. The burr-support post 404 and handle 106 may also be molded or cast as one unitary structure or permanently attached to one another such as via a chemical adhesive, a mechanical clip, or a mechanical fastener.

Referring again to FIG. 1, the handle 106 is configured to be gripped by the medical practitioner and to provide the oscillations to the burr 102. The handle 106 provides a relatively large and stable structure to be gripped. In some embodiments, the handle 106 is generally cylindrical. The handle 106 may be tapered from a proximal end to a distal end, as discussed above, or the handle 106 may be linear (as shown in FIG. 1). The handle 106 may also integrate with a stand, a charger, or another support mechanism. This keeps the burr 102 from touching anything, so as to prevent contamination and foreign materials from being transferred to the joint from the burr 102. The handle may have a cord for connecting to a power supply or wall outlet. The battery may also be charged from the power supply or wall outlet.

Referring again to the exemplary embodiment in FIG. 1, the handle 106 is configured to receive the burr-support post 104 (and by extension, the burr 102) at a post interface. The post interface secures, captures, adheres, or otherwise attaches to the burr-support post 104. The post interface keeps the burr-support post 104 secured and aligned, so as to allow the medical practitioner to perform precise movements with the oscillating decortication burr assembly.

The handle 106 is configured to be gripped by the user. In embodiments, the handle may be covered with a soft gripping material such as, foam, rubber, latex, or gel. This type of material may aid in gripping the handle without slipping. The handle may be shaped to fit a human hand with ridges where fingers can comfortably grip. These ridges and the size of the handle may be different for different sized hands or as preferred by the practitioner.

The handle 106 may present a power button 108 or another input to begin operations. In some embodiments, the handle 106 is powered by a battery and a piezoelectric transducer. The battery and the transducer impart the oscillating motion on the burr 102 based upon the actuation of the power button 108 or other input. For example, the battery and transducer may create an oscillation of approximately 240 Hz. In other embodiments, the battery and transducer may create oscillations in the range of 100-10,000 Hz, depending on the consistency of the material to be removed, the strength of the underlying bone, the capabilities of the handle 106, and other factors. In other embodiments, the handle may be powered by alternating current electrical power, hydraulic power, pneumatic power, mechanical power, or other power source. The handle may therefore interface with a cable, line, or cord for supplying this power.

In the exemplary embodiment depicted in FIG. 1, the user input is a button 108. This button provides power to the burr assembly 100 and begins the burr 102 oscillation. The oscillation may be a setting chosen prior to powering the assembly or it may be a one setting device. In other embodiments, the user input may be a knob, switch, or roller switch with multiple settings. The user input may be used to provide different levels of oscillation from fast to slow depending on the desired speed for the particular operation. This speed may be in the range of 100-10,000 Hertz as described above, or in another range based upon the application.

Figure 5:
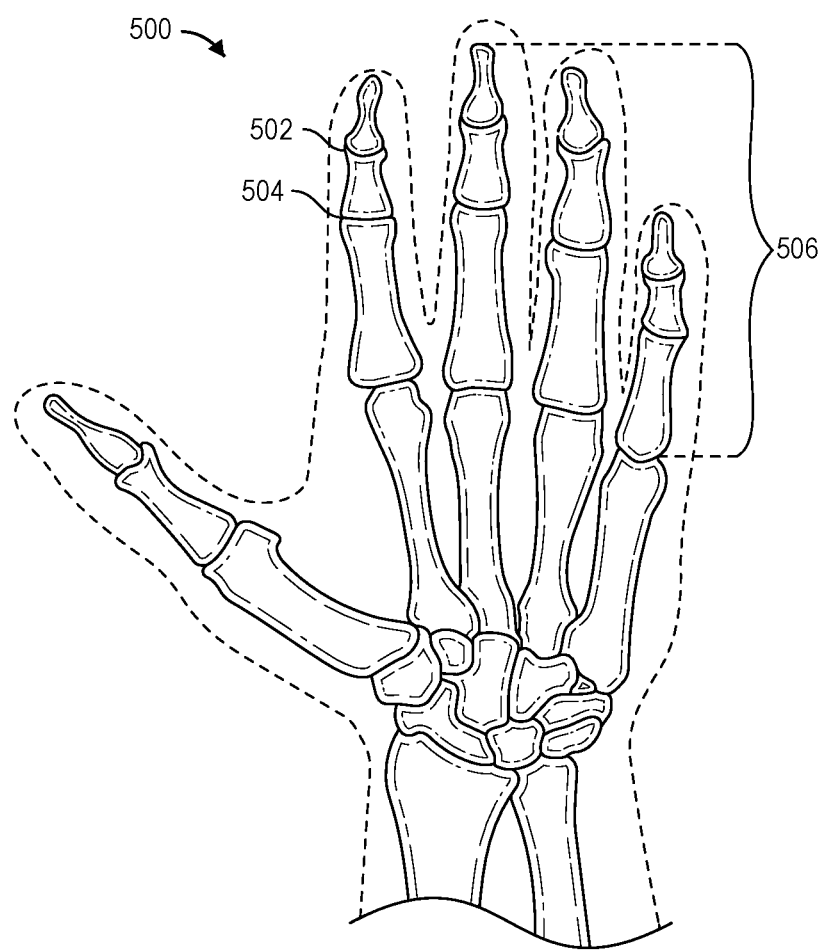
FIG. 5 depicts a skeletal hand displaying the operating joints.

A method of using the oscillating decortication burr assembly will now be discussed. The medical practitioner diagnoses arthritis of a joint. For example, FIG. 5 shows the bones 500 of the hand and fingers. Embodiments of the invention may be used to remove the articular cartilage and subchondral bone from between any of these bones. The joints of the finger (commonly known as a distal interphalangeal joint 502 and a proximal interphalangeal joint 504, located between the respective phalanges 506) may require the discussed procedure, for example.

The medical practitioner applies an anesthetic. Following the anesthetic, the medical practitioner will incise the skin and expose the joint to allow access to the joint. The medical practitioner will then retract the tissue from around the joint, such as muscles, tendons, fat, and the like. The medical practitioner is ensuring that the joint is fully exposed so as to prevent collateral trauma to the surrounding tissue. The medical practitioner may then manipulate or distract the joint to expose the space between the joint surfaces as much as necessary. While not requiring as much physical manipulation or surgical exposure as in the procedures of the prior art, some manipulation and/or compression may be necessary to expose the interior of the joint.

The medical practitioner also selects the burr 102 based upon the size and shape of the joint. In some instances, the medical practitioner may select the burr 102 before beginning the procedure, relying on standard joint sizes, approximations, X-ray scan information, external measurements, or other information. In other instances, the medical practitioner may select the burr 102 after the joint is exposed such that the medical practitioner has a more precise understanding of the size and shape of the joint. Once the burr 102 is selected, the practitioner will secure the burr-support post 104 of the selected burr 102 to the handle 106.

With the joint exposed and the burr 102 installed, the medical practitioner grasps the handle 106 of the oscillating decortication burr assembly and applies power by manipulating the user input 108. The oscillating decortication burr assembly will then begin oscillating. In some embodiments, the medical practitioner may select the speed of oscillation. This speed may be applied by the user input 108. In other embodiments, the speed of oscillation may be the same for all instances. The medical practitioner then places the oscillating burr 102 against the joint surfaces to begin removing the articular cartilage and subchondral bone therefrom. In some embodiments, the medical practitioner may insert the burr 102 into the joint surface and then apply the power so as to allow the burr 102 to be fully within the joint. The oscillating burr 102 will then remove the articular cartilage and subchondral bone in a slow and controlled manner. The medical practitioner may adjust the angles and compression placed on the burr 102 and the affected digit to remove material and achieve the alignment as desired. The flexibility and elasticity of the burr 202 may also influence the amount of articular cartilage and subchondral bone that is removed.

Upon completion, the medical practitioner will remove the burr 102 from the joint, stop the power, irrigate the joint, align the joint, and then fixate the arthrodesis site and suture the wound. When the arthrodesis site has fused successfully, the patient will experience decreased pain and increased functionality in their daily activities.

In an embodiment, a method for removing the articular cartilage and subchondral bone by decortication is disclosed. A practitioner incises the skin to allow for pulling the skin back and exposing a joint to be decorticated. When the skin is pulled back, the joint is fully exposed to allow full access and to prevent collateral trauma to the surrounding tissue.

Figure 6:
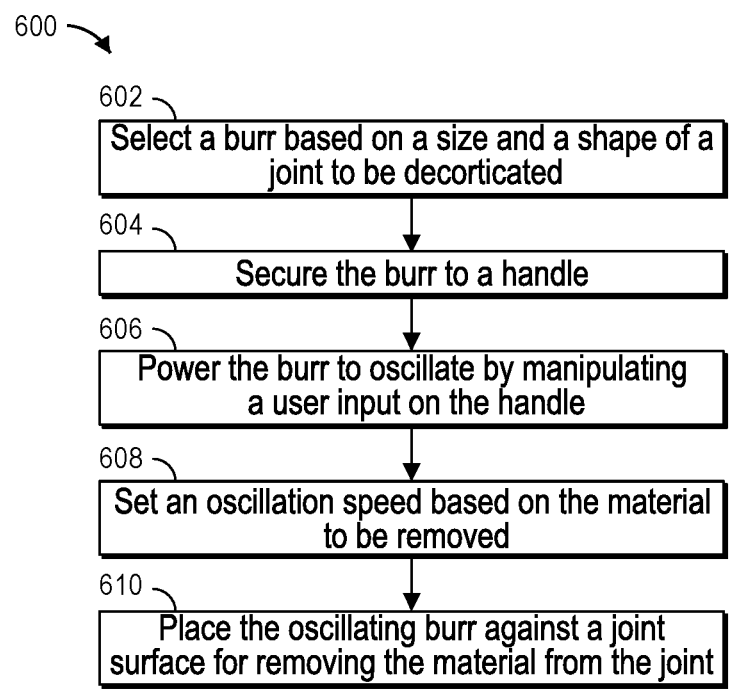
FIG. 6 depicts a method for implementing the decorticating burr assembly.

Referring to FIG. 6, exemplary steps of a method 600 are shown. In Step 602 the practitioner first selects a burr based on a size and a shape of a joint to be decorticated. In this particular embodiment, the burr is secured to a burr-support post however, this is exemplary only and the burr and post may be separate and selectively attachable. Next, in Step 604, the practitioner completes the assembly by securing the burr to the handle. This may be performed using any of the attachments described above.

In Step 606 the practitioner provides power to the assembly by manipulating the user input on the handle. The power starts the burr oscillating. In Step 608, the practitioner sets the speed of the oscillation based on the material to be removed. In Step 610, the practitioner places the oscillating burr against the joint surface. The oscillation of the burr against the material, in this case articular cartilage, causes the material to break apart from the bone. Once the operation is complete the practitioner removes the burr and stops power to the burr. The joint is then irrigated and re-aligned and the wound sutured.

It should be noted that the decortication of joints is used in this application as an exemplary field and that joints other than hand joints may be decorticated. The oscillating decortication burr assembly may be used in other fields, such as for the removal of articular cartilage and bone or other materials.

Although the invention has been described with reference to the embodiments illustrated in the attached drawing figures, it is noted that equivalents may be employed and substitutions made herein without departing from the scope of the invention.

The invention claimed is:

1. An oscillating decorticating burr system for arthrodesis comprising:
   at least one disposable burr having a semi-spherical concave shape comprising a flexible burr wall and a recess therein, wherein the semi-spherical concave shape is configured to allow the at least one disposable burr to fit within a joint space of a hand or foot, wherein the flexible burr wall is configured to conform to a shape of the joint space during use, and wherein the at least one disposable burr is configured to oscillate to remove articular cartilage and subchrondral bone within the joint space;
   a burr support post having a proximal end and a distal end, said distal end of the burr support post removably attached to the at least one disposable burr; and
   a handle having a proximal end and a distal end, the handle comprising an input for controlling the oscillation of the at least one disposable burr; wherein the distal end of the handle is attached to the proximal end of the burr support post.

2. The oscillating decorticating burr system of claim 1, wherein the handle further comprises an adjustable attaching mechanism for attaching the proximal end of the burr support post to the distal end of the handle at multiple different angles with respect to a longitudinal axis.

3. The oscillating decorticating burr system of claim 1, wherein the at least one disposable burr comprises a plurality of disposable burrs, wherein each disposable burr has a different size, a different shape, or both a different size and a different shape.

4. The oscillating decorticating burr system of claim 3, wherein the plurality of disposable burrs comprises a first burr having a diameter of 5-50 mm and a second burr having a diameter of 50-100 mm.

5. The oscillating decorticating burr system of claim 3, wherein the plurality of disposable burrs comprises a first burr having a first diameter, a second burr having a second diameter, and a third burr having a third diameter.

6. The oscillating decorticating burr system of claim 3, wherein the plurality of disposable burrs comprises a first burr having a first thickness, a second burr having a second thickness, and a third burr having a third thickness.

7. The oscillating decorticating burr system of claim 1, wherein the input of the handle allows a user to control the oscillation of the burr within a range of 100-5,000 Hz.

8. The oscillating decorticating burr system of claim 1, wherein the input of the handle comprises a button with a plurality of oscillation speed settings.

9. The oscillating decorticating burr system of claim 8, wherein one of the plurality of oscillation speed settings is 240 Hz.

10. An oscillating decorticating burr system for arthrodesis comprising:
    at least one burr having a semi-spherical concave shape comprising a flexible burr wall and a recess therein having an inner face and an outer face, wherein the flexible burr wall comprises a roughened outer surface on the inner face and the outer face wherein the semi-spherical concave shape is configured to allow the at least one burr to fit within a joint space of a hand or foot, wherein the flexible burr wall is configured to conform to a shape of the joint space during use, and wherein the at least one burr is configured to oscillate to remove articular cartilage and subchrondral bone within the joint space;
    a burr support post having a proximal end and a distal end, said distal end of the burr support post attached to the at least one burr; and
    a handle having a proximal end and a distal end, and a switch for controlling an oscillation of the at least one burr, wherein the distal end of the handle is attached to the proximal end of the burr support post.

11. The oscillating decorticating burr system of claim 10, wherein said switch comprises a plurality of oscillation speed settings.

12. The oscillating decorticating burr system of claim 11, wherein the plurality of oscillation speed settings is within a range of 100-10,000 Hz.

13. The oscillating decorticating burr system of claim 12, wherein one of the plurality of oscillation speed settings is 240 Hz.

14. A method for removing articular cartilage and subchondral bone by decortication comprising:
    providing a plurality of disposable burrs, wherein each burr has a different size, a different shape, or both a different size and a different shape;
    selecting a burr from the plurality of disposable burrs based on a size and a shape of a joint space of a particular patient;
    attaching the selected burr to a handle;
    selecting an oscillating speed using a control on the handle to cause the burr to oscillate, wherein the oscillating speed is based on a material to be removed;
    inserting the burr into the joint space; and
    placing the burr against a joint surface to remove articular cartilage or subchrondral bone from the joint.

15. The method of claim 14, wherein attaching the selected burr to the handle comprises:
    providing a burr support post having a distal end and a proximal end, attaching the distal end of the burr support post to the selected burr, and attaching the proximal end of the burr support post to the handle such that an angle of the burr support post is adjustable.

16. The method of claim 14, wherein the selected oscillating speed is within a range of 100-10,000 Hz.

17. The method of claim 14, wherein the selected oscillating speed is below 5,000 Hz.

18. The method of claim 14, wherein the selected oscillating speed is 240 Hz.

19. The method of claim 14, wherein the plurality of disposable burrs comprises a first burr having a first thickness, a second burr having a second thickness, and a third burr having a third thickness.

* * * * *